United States Patent
Kawamura (10) Patent No.: US 6,524,273 B2
(45) Date of Patent: Feb. 25, 2003

(54) NO-NEEDLE BLOOD ACCESS DEVICE FOR HEMODIALYSIS

(76) Inventor: Akio Kawamura, 2-75, Tsukisamu-Nishi 2-jo, 10-chome, Toyohira-ku, Sapporo-shi (JP)

( * ) Notice: Subject to any disclaimer, the term of this patent is extended or adjusted under 35 U.S.C. 154(b) by 0 days.

(21) Appl. No.: 09/851,326

(22) Filed: May 9, 2001

(65) Prior Publication Data

US 2001/0049488 A1 Dec. 6, 2001

(30) Foreign Application Priority Data

May 29, 2000 (JP) ........................................ 2000-158626

(51) Int. Cl.$^7$ ............................................. A61M 37/00
(52) U.S. Cl. ................... 604/93.01; 604/175; 604/6.16; 604/7
(58) Field of Search ................. 604/288.01, 288.02, 604/288.03, 288.04, 8, 9, 93.01, 94.01, 174, 4.01, 7, 248, 175, 6.16, 249, 33

(56) References Cited

U.S. PATENT DOCUMENTS

| | | | | |
|---|---|---|---|---|
| 3,626,938 A | * | 12/1971 | Versaci | 137/625.47 |
| 4,306,545 A | * | 12/1981 | Ivan et al. | 128/887 |
| 4,443,214 A | * | 4/1984 | Marion | 604/10 |
| 4,496,350 A | | 1/1985 | Cosentino | |
| 4,822,341 A | * | 4/1989 | Colone | 604/175 |
| 4,898,669 A | * | 2/1990 | Tesio | 137/625.47 |
| 5,466,228 A | * | 11/1995 | Evans | 137/625.47 |
| 5,643,194 A | * | 7/1997 | Negre | 137/385 |
| 5,916,201 A | * | 6/1999 | Wilson et al. | 137/625.41 |
| 5,968,011 A | * | 10/1999 | Larsen et al. | 604/164.01 |
| 6,231,541 B1 | * | 5/2001 | Kawamura | 604/175 |
| 6,269,704 B1 | * | 8/2001 | Ziv et al. | 600/573 |

FOREIGN PATENT DOCUMENTS

JP 2983540 B1 9/1999

* cited by examiner

Primary Examiner—Brian L. Casler
Assistant Examiner—Mark Han
(74) Attorney, Agent, or Firm—Griffin & Szipl, P.C.

(57) ABSTRACT

A no-needle blood access device for hemodialysis including a cylindrical external body (20), the lower portion of the external body being provided with openings (28) at diametrically facing locations. Pipe members (30) are mounted in the respective openings. First and second artificial conduits (12, 14) are fitted into the respective pipe member, each of the artificial conduits being anastomosed to a targeted artery or vein; and a columnar internal body (40) fitted into the external body so as to be rotated in the external body. The device is arranged such that, when the internal body is rotated so that a first through-hole (42) communicates with the openings (28), the first artificial conduit (12) is in communication with the second artificial conduit (14) through the first through-hole (42), and when the internal body is rotated so that a first position (44) mates with one of the openings and a third position (50) mates with the other of the openings, a second through-hole is in communication with the first artificial conduit (12) and the third through-hole is in communication with the second artificial conduit (14).

8 Claims, 7 Drawing Sheets

NO-NEEDLE BLOOD ACCESS DEVICE FOR HEMODIALYSIS

BACKGROUND OF THE INVENTION

The present invention generally relates to a no-needle blood access device for hemodialysis. More specifically, the present invention relates to a no-needle blood access device for hemodialysis which has a mechanism of simple structure and does not need a caregiver.

DESCRIPTION OF THE PRIOR ART

Hemodialysis is used widely as a remedy for treating kidney insufficiency. In many cases, a surgical short circuit which is commonly referred to as "shunt " is implanted in a blood vessel or blood vessels of the patient suffering from serious kidney disease, because such a patient must receive hemodialysis treatment periodically over a long period of time. Shunts are divided broadly into two categories, an internal shunt and an external shunt. The internal shunt has a drawback that needle puncture is required during hemodialysis. On the other hand, the external shunt has a high rate of thrombosis and infection, and makes daily life more inconvenient.

To overcome these drawbacks of the prior shunts, as described in U.S. Pat. No. 4,496,350, a blood access device for hemodialysis given the tradename "Hemasite" has been developed. This Hemasite blood access device has an advantage that needle puncture is not required, but due to its complicated structure, is costly and troublesome to handle.

Taking into consideration such circumstances, the applicant of the present invention has proposed a novel blood access device for hemodialysis in Japanese Patent No. 2983540 which corresponds to U.S. patent application Ser. No. 09/307,716 filed on May 10, 1999. This blood access device is very useful for the patient because it does not require needle puncture, and has a mechanism of simple structure, and can be manufactured at a relatively low cost, and is easy to handle. However, in the device, a caregiver is required during the beginning and the completion of the hemodialysis and thus, it is very desirable to have a blood access device for hemodialysis which does not need a caregiver, while maintaining the above described advantages.

SUMMARY OF THE INVENTION

It is therefore an object of the present invention to provide a blood access device for hemodialysis which does not require needle puncture, and which has a mechanism of simple structure, and which can be manufactured at a relatively low cost, and which is easy to handle, and which does not need a caregiver during hemodialysis.

The above and other objects of the present invention can be accomplished by a no-needle blood access device for hemodialysis comprising, a cylindrical external body, the external body including a peripheral wall and a bottom wall and opens to its top, the lower portion of the external body being provided with openings at locations diametrically facing with respect to each other, each of pipe members being mounted on the respective openings, each of first and second artificial conduits being fitted into the respective pipe member, each of the artificial conduits being anastomosed to a targeted artery or vein; and a columnar internal body fitted into the external body so as to be rotated in the external body, the internal body being provided with a first through-hole diametrically extending through the internal body in the horizontal direction at the location having a height on which the openings are mounted; the internal body being provided with a second through-hole extending between a first position spaced at an angular distance of $\alpha$ degrees ($\alpha$:acute angle) clockwise from the first through-hole in an outer surface of the internal body and having a height substantially equal to a height at which the opening locates, and a second position spaced at an angular distance of $\alpha$ degrees clockwise from the first through-hole in a top surface of the internal body, the internal body being also provided with a second through-hole extending between a third position spaced at an angular distance of $\beta$ degrees ($\beta=180°-\alpha$) counterclockwise from the first through-hole in the outer surface of the internal body and having a height substantially equal to a height at which the opening locates, and a fourth position spaced at an angular distance of $\beta$ degrees counterclockwise from the first through-hole in the top surface, whereby the device is arranged such that, when the internal body is rotated so that the first through-hole communicates with the openings, the first artificial conduit is in communication with the second artificial conduit through the first through-hole, and when the internal body is rotated so that the first position mates with one of the openings and the third position mates with the other of the openings, the second through-hole is in communication with the first artificial conduit and the third through-hole is in communication with the second artificial conduit.

In a preferred aspect of the present invention, a cannula assembly connected to a dialyzer is further provided, the cannula assembly including a disk provided with a pair of through-holes at side by side position, a first pair of cannulas connected to one end of the through-holes of the disk respectively so as to be in communication with the through-holes of the disk, and a second pair of cannulas connected to the other end of the through-holes of the disk so as to be in communication with the through-holes of the disk, whereby each of the first pair of the cannulas assembly is inserted into the second and third through-holes of the internal body, and the internal body is rotated in the external body so that the second through-holes communicates with the first artificial conduit and the third through-holes communicates with the second artificial conduit to effect hemodialysis.

In another preferred aspect of the present invention, the degree $\alpha$ is 90°.

In a further preferred aspect of the present invention, finger grips for rotating the internal body are provided at the top surface of the internal body.

In a further preferred aspect of the present invention, the inner height of the external body is selected to be substantially equal to the sum of the height of the internal body and the height of the disk of the cannula assembly.

The above and other objects and features of the present invention will become apparent from the following description made with reference to the accompanying drawings.

DESCRIPTION OF THE PREFERRED EMBODIMENTS

The preferred embodiments of the present invention will now be explained with reference to the accompanied drawings. A no-needle blood access device for hemodialysis generally indicated by a reference numeral 10 in FIG. 1 which is an embodiment of the present invention comprises a cylindrical external body 20. The external body 20 includes a peripheral wall 22 and a bottom wall 24 and opens to the top. The external body 20 defines a well 26 therein. The lower portion of the peripheral wall 22 is provided with openings 28 at locations diametrically facing with respect to each other, and each of the pipe members 30 is mounted on the respective openings 28.

Preferably, the external body 20 is made from titanium which is light and biocompatible, and the part of the body 20 with which blood comes into contact is covered with pyrolitic carbon which is an anticoagulant substance. Further, preferably, the external surface of the peripheral wall 22 and the bottom wall 24 of the external body 20 is covered with a biocompatible fiber 32 such as dacron velour in order to enhance the fusion with human tissue and provide a barrier to bacteria invading from the outside.

Each of artificial conduits 12 and 14 is fitted into the respective pipe members 30 mounted on the peripheral wall 22 of the external body 20, whereby the well 26 is in communication with the artificial conduits 12 and 14 through the openings 28 and the pipe members 30. Serration 31 is provided at the external surface of each of the pipe members 30 to prevent the artificial conduits 12 and 14 fitted into the pipe members 30 from being disconnected.

The blood access device 10 further comprises a columnar internal body 40 fitted into the inside of the external body 20. The internal body 40 has an outer diameter slightly smaller than an inner diameter of the external body 20 and the internal body 40 can be rotated in the external body 20. Preferably, to facilitate the rotation of the internal body 40, a columnar projection 24a is provided at the center of the bottom wall 24 of the inside of the external body 20, and a recess 40a having a shape complementary to the projection 24a is provided at the center of the bottom of the internal body 40.

Figure 3:
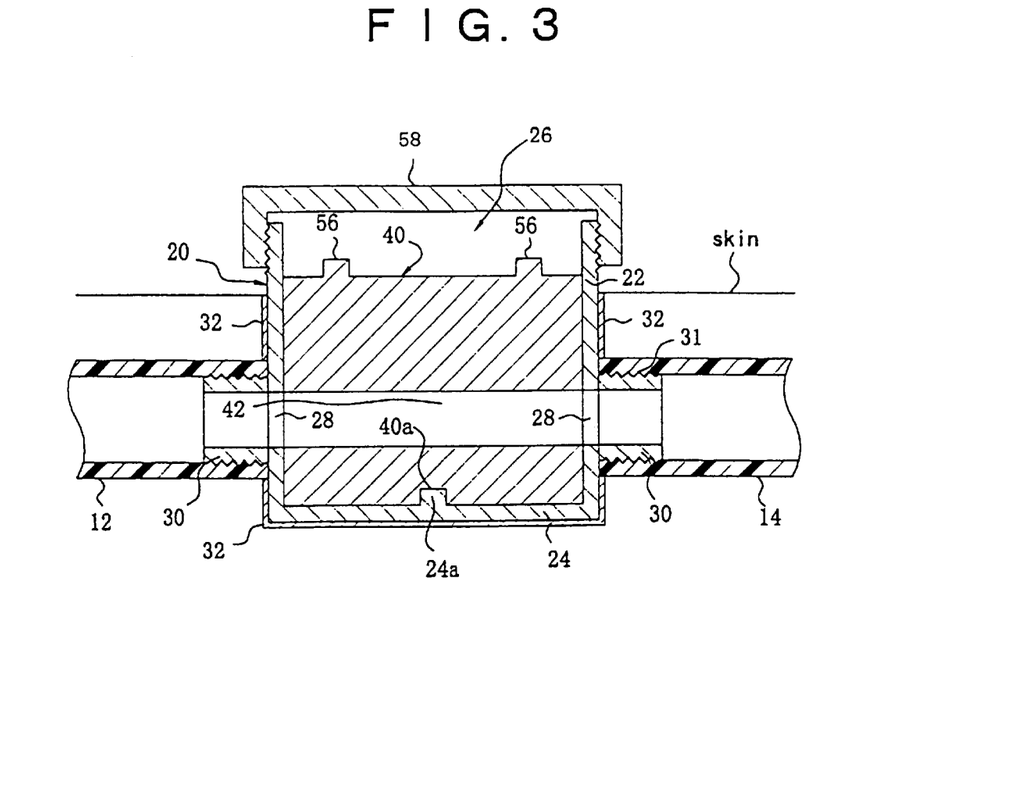
FIG. 3 is a cross sectional view of the device of FIG. 1 showing the condition wherein each of the artificial conduits is in communication with the first through-hole.
Figure 5:
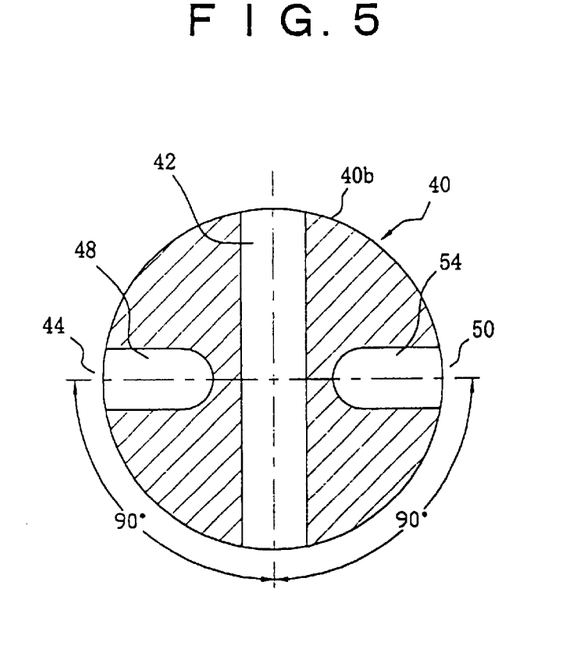
FIG. 5 is a cross sectional view taken in the height at which the first through-hole locates.
Figure 6:
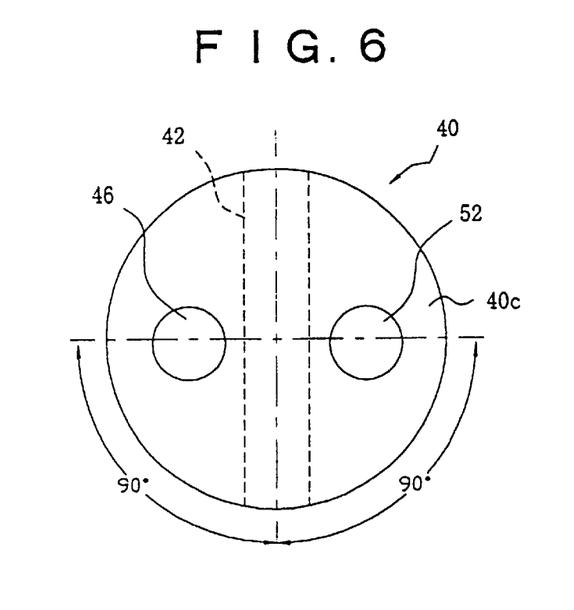
FIG. 6 is a plan view of the internal body.

As best shown in FIGS. 3 and 5, the internal body 40 is provided with a first through-hole 42 diametrically extending through the internal body 40 in the horizontal direction at the location having a height similar to a height on which the openings 28 are mounted.

The internal body 40 is provided with a second through-hole 48 extending between a first position 44 spaced at an angular distance of 90 degrees clockwise from the first through-hole 42 in an outer surface 40b of the internal body 40 and having a height substantially equal to a height at which the opening 28 locates when the internal body 40 is fitted into the external body 20 (in other words, a height at which the first through-hole 42 is provided), and a second position 46 spaced at an angular distance of 90 degrees clockwise from the first through-hole 42 in a top surface 40c of the internal body. The internal body 40 is also provided with a second through-hole 48 extending between a third position 50 spaced at an angular distance of 90 degrees counterclockwise from the first through-hole 42 in an outer surface 40b of the internal body 40 and having a height substantially equal to a height at which the opening 28 locates when the internal body 40 is fitted into the external body 20 (in other words, a height at which the first through-hole 42 is provided), and a fourth position 52 spaced at an angular distance of 90 degrees counterclockwise from the first through-hole 42 in the top surface 40c. As shown in FIG. 5, the second and third through-holes 48 and 50 are symetric with respect to the first through-holes 42.

Figure 4:
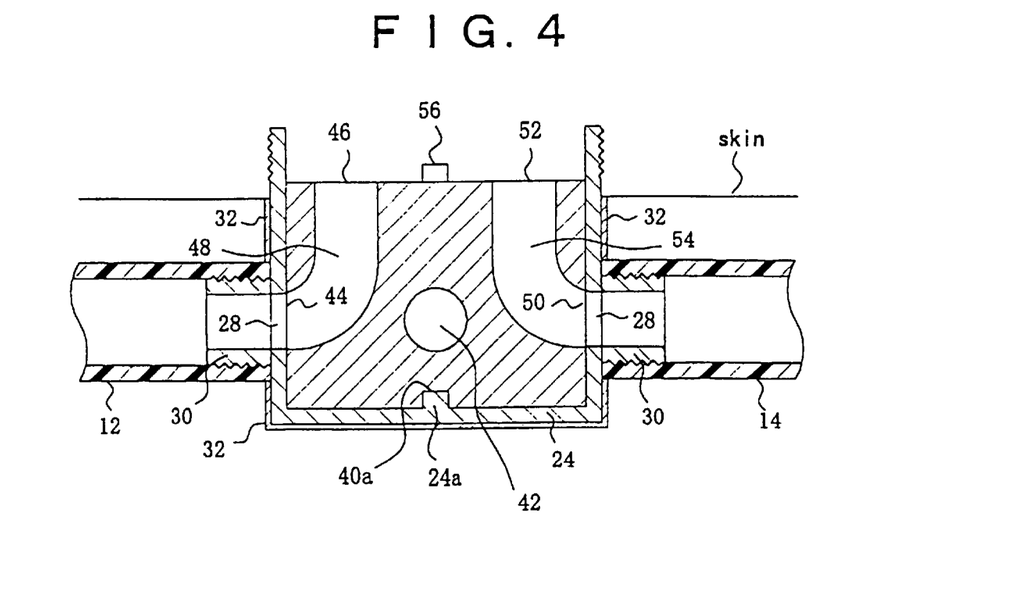
FIG. 4 is a cross sectional view of the device of FIG. 1 showing the condition wherein each of the artificial conduits is in communication with the second and third through-holes respectively.

From the above construction, as shown in FIG. 3, when the internal body 40 is rotated so that the first through-hole 42 communicates with the openings 28, the artificial conduit 12 is in communication with the artificial conduit 14. On the other hand, as shown in FIG. 4, when the internal body 40 is rotated so that the first position 44 mates with one of the openings 28 (in other words, so that the third position 50 mates with the other of the openings 28), the second through-hole 48 communicates with the artificial conduit 12 and the third through-hole 54 communicates with the artificial conduit 14.

Preferably, the internal body 40 is made of polytetrafluoroethylene such as Teflon. Further, preferably, the top surface 40c of the internal body 40 is provided with finger grips 56 for rotating the internal body 40.

Further, the top of the external body 20 is covered with a cap 58 when the blood access device 10 is not in use.

Figure 8:
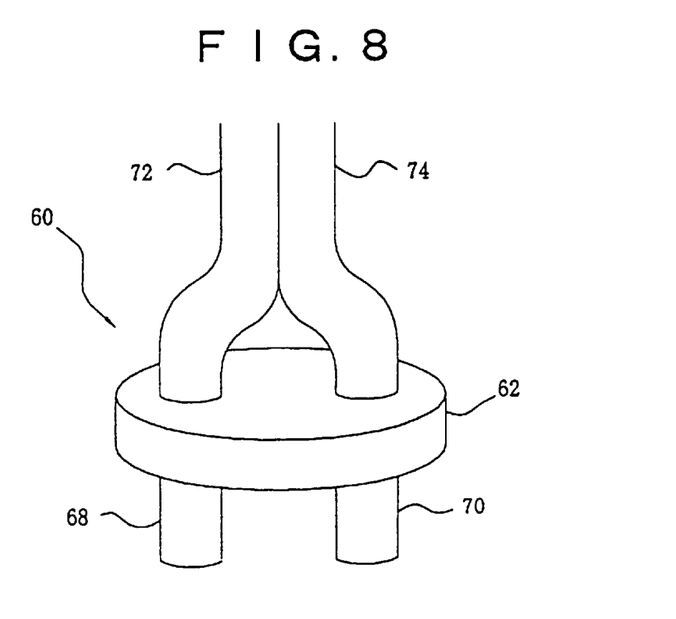
FIG. 8 is a perspective view showing a cannula assembly.
Figure 9:
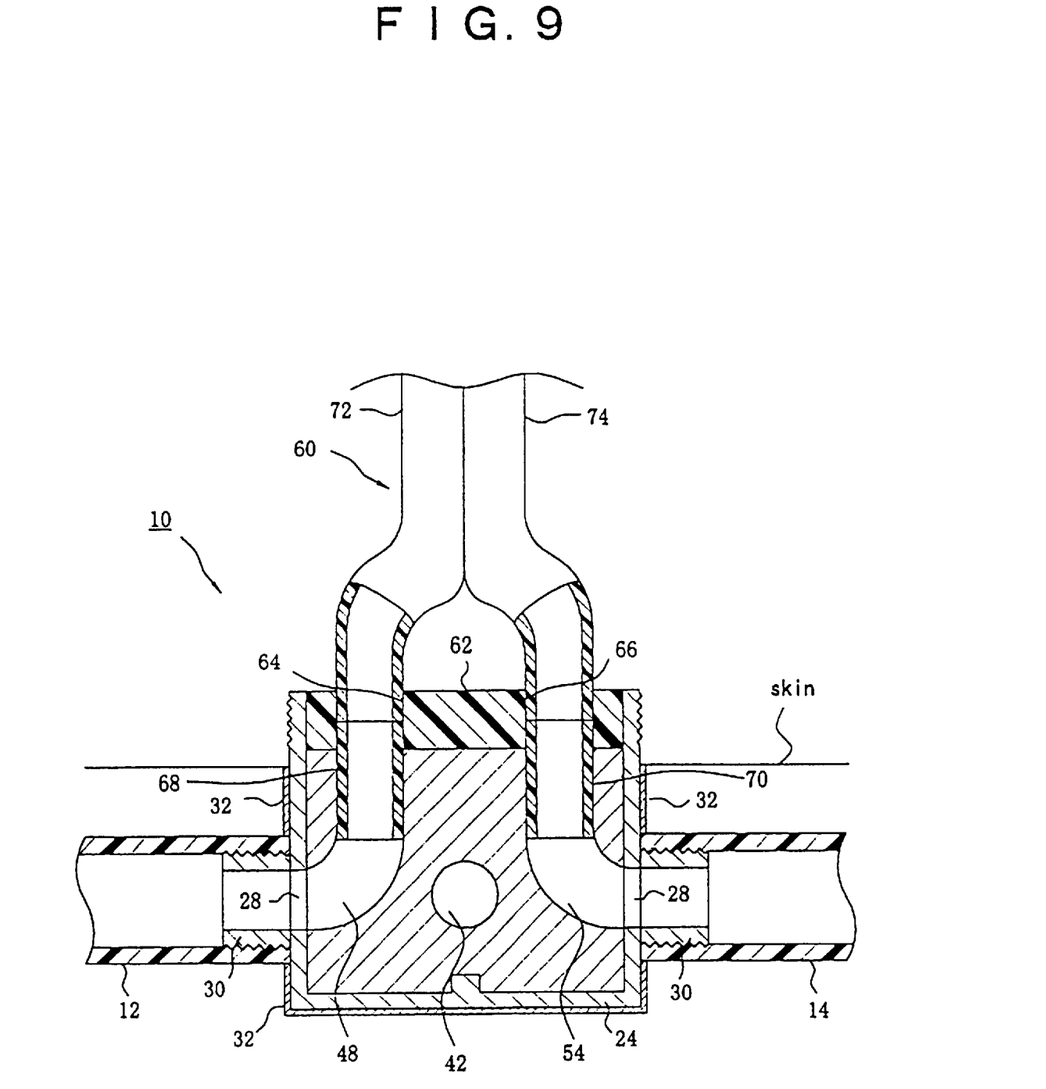
FIG. 9 is a cross sectional view showing the condition wherein the cannula assembly is in communication with the artificial conduits.
Figure 10:
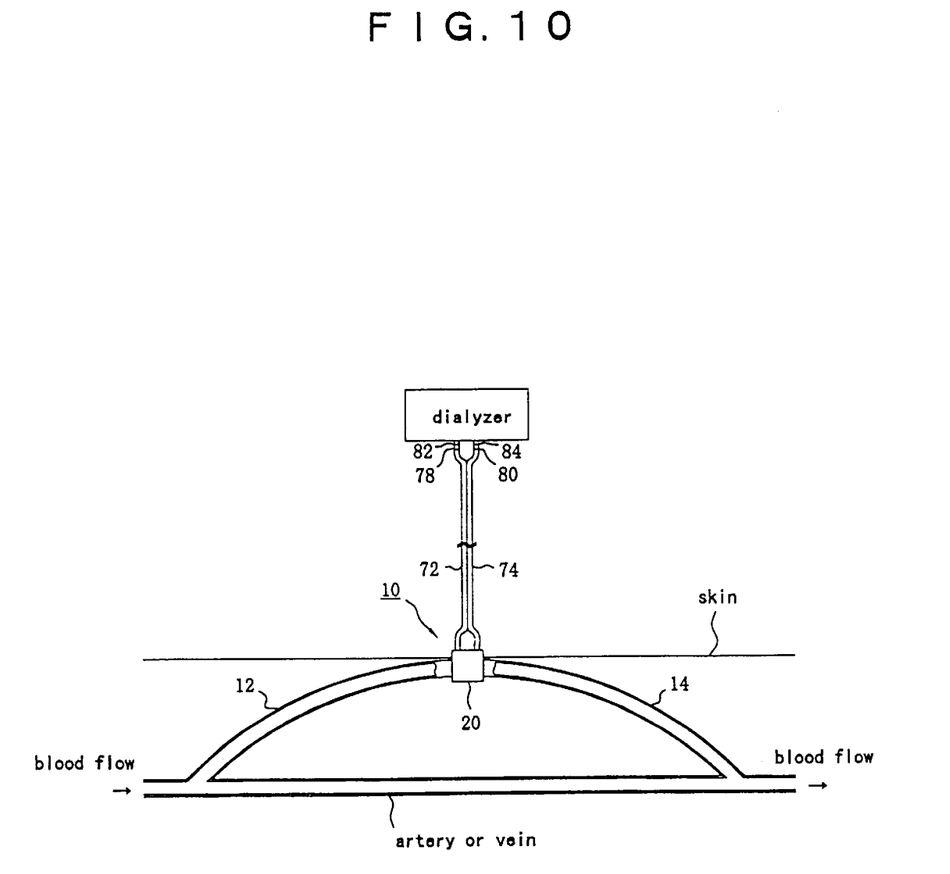
FIG. 10 is a diagrammatic view showing the condition wherein the no-needle blood access device for hemodialysis of the present invention is used to hemodialyze.

The blood access device 10 further comprises a cannula assembly 60 connected to a dialyzer. As shown in FIGS. 8 and 9, the cannula assembly 60 includes a disk 62 provided with a pair of through-holes 64 and 66 at side by side position, a pair of cannulas 68 and 70 connected to one end of the through-holes 64 and 66 respectively so as to be in communication with the through-holes 64 and 66, and a pair of cannulas 72 and 74 connected to the other end of the through-holes 64 and 66 so as to be in communication with the through-holes 64 and 66. The cannulas 68, 70, 72 and 74 are made of a conventional flexible material, and the disk 62 is made of a plastic material or a rubber material.

Preferably, the diameter of the disk 62 is selected to be slightly smaller than the inner diameter of the external body 20 to facilitate the insertion of the disk 62 into the external body 20 during hemodialysis. Further, the space of the cannulas 68 and 70 is selected so that each of the leading ends of the cannulas 68 and 70 is inserted into the second through-hole 48 and the third through-hole 54 when the disk 62 is fitted into the external body 20. Furthermore, the space of the through-holes 64 and 66 of the disk 62 (in other words, the space of the cannulas 68 and 70) is selected to be substantially equal to the space of the second and third through-holes 48 and 54 in the top surface 40c of the internal body 40.

The diameter of each of the leading ends of the cannulas 68 and 70 (in other words, the ends which are inserted into the second and third through-hole 48 and 54) is selected to be slightly smaller than the diameter of each of the second and third through-hole 48 and 54 to facilitate the insertion of the cannulas into the second and third through-hole 48 and 54.

Preferably, the inner height of the external body 20 is selected to be substantially equal to the sum of the height of the internal body 40 and the height of the disk 62 of the cannula assembly 60.

The cannulas 72 and 74 are tubes adapted to define a connecting circuit leading to the dialyzer, and each of them has an internal diameter approximately equal to the internal diameter of each of the cannulas 68 and 70. The cannula 72 is provided at the end proximal to the dialyzer with a terminal 78 for connecting to a terminal 82 of the dialyzer. The cannula 74 is also provided at the end proximal to the dialyzer with a terminal 80 for connecting to a terminal 84 of the dialyzer. Each of the terminals 78 and 80 may be a conventional screw type terminal. Each of the cannulas 72 and 74 has a length (at least 3 meters) sufficient for the patient to move around with relative freedom during hemodialysis. Since the internal diameter of each of the cannulas 72 and 74 is selected to be approximately equal to that of each of the canulas 68 and 70 as described above, the length of each of the cannulas 72 and 74 can be insured without increasing the amount of blood circulating outside the body of the patient.

The cannulas 72 and 74 may consist of either two separate tubes, or one tube in appearance which is made by combining two tubes as shown in FIGS. 8 and 9.

Figure 1:
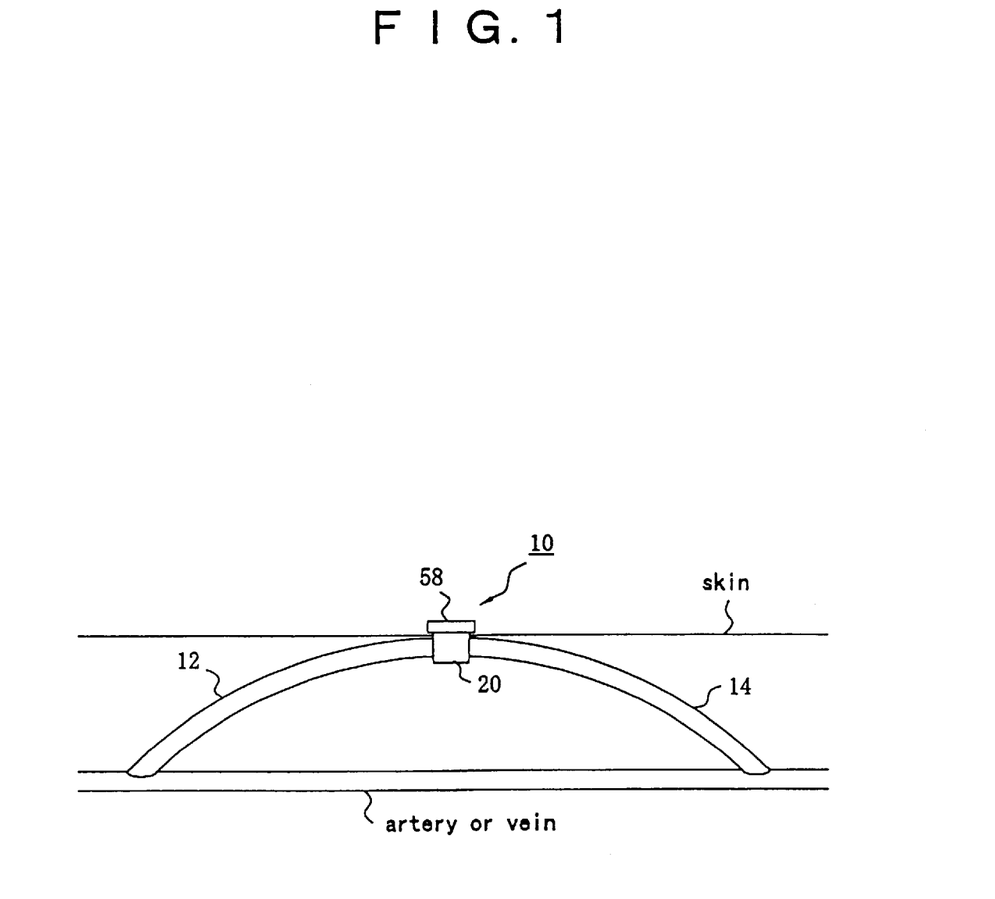
FIG. 1 is a diagrammatic view of a no-needle blood access device for hemodialysis of a preferred embodiment of the present invention which is implanted in a human body.
Figure 2:
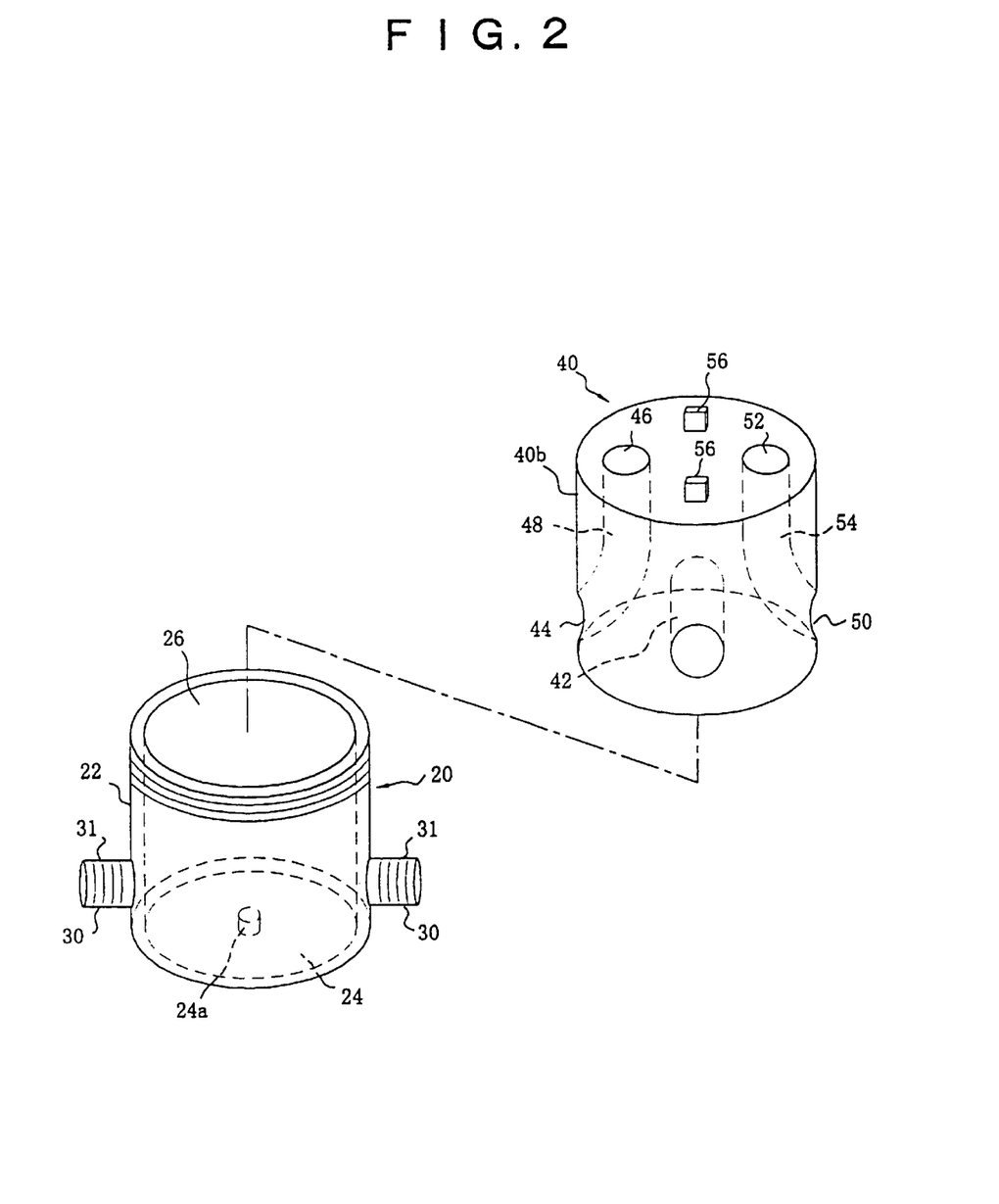
FIG. 2 is an exploded view of the no-needle blood access device for hemodialysis of FIG. 1.

The thus constituted no-needle blood access device for hemodialysis 10 operates as follows. Firstly, as shown in FIG. 1, the device 10 is implanted in a desired area of the upper arm, etc. of the patient and each of the artificial conduits 12 and 14 is anastomosed to the targeted artery or vein. When it is to be hemodialyzed, the cap 58 is removed from the body 20, and each of the cannulas 68 and 70 of the cannula assembly 60 which is connected to the dialyzer is inserted into the second and third through-holes 48 and 54 of the internal body 40. Thereafter, as shown in FIG. 9, the internal body 40 is rotated in the external body 20 so that the second through-holes 48 communicates with the artificial conduit 12 and the third through-holes 54 communicates with the artificial conduit 14, and hemodialysis is effected. When hemodialysis is completed, the internal body 40 is rotated so that the first through-holes 42 is in communication with each of the artificial conduits 12 and 14. Then, each of the cannulas 68 and 70 is withdrawn, and the external body 20 is covered with the cap 58.

The present invention has thus been shown and described with reference to specific embodiments. However, it should be noted that the present invention is in no way limited to the details of the described arrangements but changes and modification may be made without departing from the scope of the appended claims.

Figure 7:
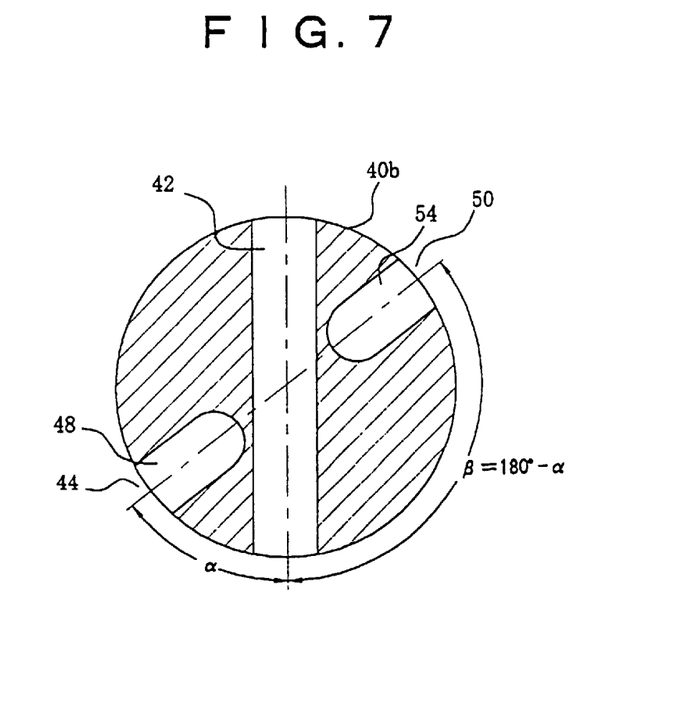
FIG. 7 is a cross sectional view similar to FIG. 5 showing another version of the second and third through-holes.

For example, although each of the second and third through-holes 48 and 54 is provided at a position spaced at an angular distance of 90 degrees from the first through-hole 42 in the above described embodiments, the second through-hole 48 may be provided at a position spaced at an angular distance of α degrees(α: acute angle) clockwise from the first through-hole 42, and the third through-hole 54 may be provided at a position spaced at an angular distance of β degrees(β=180° −α) counterclockwise from the first through-hole 42, as shown in FIG. 7.

Further, although the projection 24a is provided at the center of the bottom wall 24 of the external body 20 and the recess 40a is provided at the bottom of the internal body 40 in the above described embodiments, the projection may be provided at the bottom of the internal body and the corresponding recess may be provided at the bottom wall 24 of the external body 20.

Further, although each of the cannulas 68 and 72 is made of two separate tubes and each of the cannulas 70 and 74 is also made of two separate tubes in the above described embodiments, the cannulas 68 and 72 may be made of one tube and the cannulas 70 and 74 may be also made of one tube. Furthermore, each of the artificial conduits is anastomosed to the same artery or vein in the above described embodiments, each of them may be anastomosed to separate arteries or veins.

According to the present invention, since the artery or vein can be in communication with the dialyzer by simply rotating the internal body 40, hemodialysis can be effected without a caregiver. Further, since the body has a simple structure, the blood access device for hemodialysis which does not require needle puncture and can be manufactured at a relatively low cost and is easy to handle, is provided.

What is claimed is:

1. A no-needle blood access device for hemodialysis comprising:

a cylindrical external body, the external body including a peripheral wall and a bottom wall and opens to a top portion, a lower portion of the external body being provided with openings at locations diametrically facing with respect to each other, a pipe member being mounted respectively on each one of the openings, each of first and second artificial conduits being fitted into one of the pipe members, each of the first and second artificial conduits being anastomosed to a targeted artery or vein;

a columnar internal body fitted into the external body so as to be rotated in the external body, the internal body being provided with a first through-hole diametrically extending through the internal body in the horizontal direction at a location having a height similar to a height of the locations of the openings on the external body;

the internal body being provided with a second through-hole extending between a first position spaced at an angular distance of α degrees clockwise from the first through-hole in an outer surface of the internal body and having a height substantially equal to the height of the locations of the openings, and a second position spaced at an angular distance of α degrees clockwise from the first through-hole in a top surface of the internal body, the internal body being also provided with a third through-hole extending between a third position spaced at an angular distance of β degrees counterclockwise from the first through-hole in the outer surface of the internal body and having a height substantially equal to the height of the locations of the openings, and a fourth position spaced at an angular distance of β degrees counterclockwise from the first through-hole in the top surface, wherein β=180°−α, whereby the device is arranged such that, when the internal body is rotated so that the first through-hole communicates with the openings, the first artificial conduit is in communication with the second artificial conduit through the first through-hole, and when the internal body is rotated so that the first position mates with one of the openings and the third position mates with another one of the openings, the second through-hole is in communication with the second artificial conduit; and a cannula assembly connected to a dialyzer, the cannula assembly including:
  a disk provided with a pair of through-holes at a side-by-side position;
  a first pair of cannulas connected respectively to one end of one of the through-holes of the disk so as to be in communication with the through-holes of the disk; and
  a second pair of cannulas connected to the other end of the through-holes of the disk so as to be in communication with the through-holes of the disk, whereby each cannula of the first pair of cannulas is inserted into a respective one of the second and third through-holes of the internal body, and the internal body rotates in the external body so that the second through-hole communicates with the first artificial conduit and the third through-hole communicates with the second artificial conduit to effect hemodialysis.

2. A no-needle blood access device for hemodialysis in accordance with claim 1, wherein the degree α is 90°.

3. A no-needle blood access device for hemodialysis in accordance with claim 2, wherein finger grips for rotating the internal body are provided at the top surface of the internal body.

4. A no-needle blood access device for hemodialysis in accordance with claim 2, wherein an inner height of the external body is selected to be substantially equal to the sum of a height of the internal body and a height of the disk of the cannula assembly.

5. A no-needle blood access device for hemodialysis in accordance with claim 2, wherein an inner height of the external body is selected to be substantially equal to the sum of a height of the internal body and a height of the disk of the cannula assembly.

6. A no-needle blood access device for hemodialysis in accordance with claim 1, wherein finger grips for rotating the internal body are provided at the top surface of the internal body.

7. A no-needle blood access device for hemodialysis in accordance with claim 6, wherein an inner height of the external body is selected to be substantially equal to the sum of a height of the internal body and a height of the disk of the cannula assembly.

8. A no-needle blood access device for hemodialysis in accordance with claim 1, wherein an inner height of the external body is selected to be substantially equal to the sum of a height of the internal body and a height of the disk of the cannula assembly.

* * * * *